US011045186B2

(12) United States Patent
Belman et al.

(10) Patent No.: US 11,045,186 B2
(45) Date of Patent: Jun. 29, 2021

(54) ENDOSCOPIC SUTURING NEEDLE LOADER DEVICE, SYSTEM AND METHOD

(71) Applicant: BOSS INSTRUMENTS, LTD., INC., Gordonsville, VA (US)

(72) Inventors: Yuri Belman, Campbell, CA (US); Alexander Borisovich Zatyuryukin, Moscow (RU); Patricia A. Moore, Incline Village, NV (US)

(73) Assignee: BOSS INSTRUMENTS, LTD., INC., Gordonsville, VA (US)

( * ) Notice: Subject to any disclaimer, the term of this patent is extended or adjusted under 35 U.S.C. 154(b) by 288 days.

(21) Appl. No.: 16/200,755

(22) Filed: Nov. 27, 2018

(65) Prior Publication Data
US 2019/0117215 A1  Apr. 25, 2019

Related U.S. Application Data

(63) Continuation of application No. 14/773,978, filed as application No. PCT/US2014/023711 on Mar. 11, 2014, now abandoned.
(Continued)

(51) Int. Cl.
*A61B 17/04* (2006.01)
*A61B 17/062* (2006.01)
(Continued)

(52) U.S. Cl.
CPC ........ *A61B 17/0469* (2013.01); *A61B 17/062* (2013.01); *A61B 17/0625* (2013.01);
(Continued)

(58) Field of Classification Search
CPC .............. A61B 17/0469; A61B 17/062; A61B 17/0625; A61B 2017/2927; A61B 2017/0608
See application file for complete search history.

(56) References Cited

U.S. PATENT DOCUMENTS 5,665,096 A  9/1997  Yoon
5,897,563 A  4/1999  Yoon et al.
(Continued)

FOREIGN PATENT DOCUMENTS

WO    WO 2011163634 A1   12/2011

OTHER PUBLICATIONS

Extended European Search Report dated Jun. 12, 2019 in EP 11192491.6.

*Primary Examiner* — Katherine M Rodjom
(74) *Attorney, Agent, or Firm* — Nixon & Vanderhye, P.C.

(57) ABSTRACT

Improved medical suturing devices, systems, and methods for loading a needle in a suturing device, particularly standard surgical needles. An exemplary device includes a body having one or more clamps for grasping a needle and a needle loader supporting the needle in a delivery position suitable for advancing through a minimally invasive aperture and a needle loading position suitable for grasping with a clamp of the device. Preferably, the needle loader includes an elongate body having a rotatable needle holding member and is releasably coupleable with the device body such that the needle is moveable between positions from a proximal portion of the device. Methods includes selecting a standard surgical needle, advancing the needle loader device into a body of a patient, and moving the needle to a needle loading position for grasping and suturing with one or more clamps of the device.

44 Claims, 14 Drawing Sheets

Related U.S. Application Data

(60) Provisional application No. 61/778,089, filed on Mar. 12, 2013.

(51) Int. Cl.
    *A61B 17/06*     (2006.01)
    *A61B 17/29*     (2006.01)
    *A61B 17/00*     (2006.01)

(52) U.S. Cl.
    CPC ............... *A61B 2017/0053* (2013.01); *A61B 2017/0608* (2013.01); *A61B 2017/2927* (2013.01)

(56) References Cited

U.S. PATENT DOCUMENTS

| | | |
|---|---|---|
| 5,938,668 A | 8/1999 | Scirica et al. |
| 5,954,733 A | 9/1999 | Yoon |
| 5,957,937 A | 9/1999 | Yoon |
| 6,071,289 A | 6/2000 | Stefanchik et al. |
| 6,126,665 A | 10/2000 | Yoon |
| 2005/0043746 A1 | 2/2005 | Pollak |
| 2006/0095052 A1* | 5/2006 | Chambers .......... A61B 17/0469 606/139 |
| 2008/0243147 A1 | 10/2008 | Hamilton |
| 2009/0287226 A1 | 11/2009 | Gellman |
| 2012/0130404 A1 | 5/2012 | Meade |
| 2012/0150199 A1 | 6/2012 | Woodard, Jr. |
| 2012/0283755 A1 | 11/2012 | Gellman |

\* cited by examiner

ENDOSCOPIC SUTURING NEEDLE LOADER DEVICE, SYSTEM AND METHOD

CROSS-REFERENCES TO RELATED APPLICATIONS

This application is a Continuation of application Ser. No. 14/773,978 filed Sep. 9, 2015, which is a U.S. national phase of Application No. PCT/US2014/023711 filed Mar. 11, 2014 which designated the U.S. and claims priority to Provisional Application No. 61/778,089 filed Mar. 12, 2013, the entire contents of each of which are hereby incorporated by reference.

The following commonly-assigned applications and patents disclose related subject matter, and are hereby incorporated herein by reference in their entirety: U.S. patent application Ser. No. 13/168,426 filed Jun. 24, 2011 and titled "Endoscopic Suturing Device, System, and Method;" U.S. patent application Ser. No. 11/532,032 filed Sep. 14, 2006 and titled "Suturing Device, System, and Method;" U.S. patent application Ser. No. 12/535,499 filed Aug. 4, 2009; U.S. patent application Ser. No. 12/049,545 filed on Mar. 17, 2009; U.S. patent application Ser. No. 12/049,552 filed on Mar. 17, 2008; and U.S. patent provisional application Ser. No. 11/227,981 filed Sep. 14, 2005.

BACKGROUND OF THE INVENTION

The present invention generally relates to medical devices, systems, and methods. In specific embodiments, the invention provides devices, systems, and methods for suturing tissues in open surgery, minimally invasive surgical procedures, robotic surgery, and the like.

Although many aspects of surgery have changed radically over the last several decades, some surgical techniques have remained remarkably constant. For example, as was true fifty years ago, suturing remains a common technique for approximation of tissues, ligation of tissues, affixing tissues together, and the like.

Suture has been used in open surgical procedures for generations to therapeutically treat diseased tissue and to close surgical access sites and other wounds. More recently, the use of minimally invasive surgical techniques has expanded, with surgical therapies often being performed at internal surgical sites. Although a wide variety of visualization techniques (including laparoscopes and other endoscopic viewing devices, fluoroscopy and other remote imaging modalities, and the like) have been developed to allow surgeons to view these internal surgical sites, and although a large variety of new tissue treatment techniques have been developed (including ultrasound techniques, electrosurgical techniques, cryosurgical techniques, and the like) and are now widely available, many modern surgical interventions continue to rely on suturing.

A wide variety of alternatives to suturing of tissues have been developed, and have gained varying degrees of acceptance in certain surgical procedures. Staples and tissue adhesives are used quite frequently in many open and minimally invasive surgical settings, and a variety of tissue welding techniques have also been proposed. Nonetheless, suturing remains ubiquitous in surgery, as suturing provides a number of advantages over many of the alternatives.

Suture's advantages include the large knowledge and skill base that surgeons have developed over the years. Additionally, a variety of off-the-shelf, pre-packaged surgical needles with suture are available from a large number of suppliers at very reasonable cost. Surgeons are able to precisely control the location of suture stitches by grasping the suture needle and first pushing it and then pulling it through the target tissue. In open surgery the surgeon may manually grasp the suture needle directly with his or her hand, although both open and minimally invasive procedures are often performed by grasping the needle with a needle grasping tool and manipulating the tool to place the suture stitches. The results obtained using suture are highly predictable, although dependent on the skill of the surgeon. In light of its advantages, the use of suture does not appear likely to disappear any time soon, with even modern robotic surgical techniques often making use of suture.

Although suture remains popular in surgery at least in part due to its significant advantages, suturing is not without disadvantages. In particular, placing a large number of suture stitches can be tiring and quite time-consuming. Manipulation of a suture needle can be difficult even in open surgery due to the limited space that is often available around the target tissues. The challenges of manipulating suture needles may be even greater in minimally invasive surgical procedures, where the needles are often manipulated using long-handled tools extending through a small aperture, typically while viewing the procedure on a display which is offset from the surgical site. Tools used in minimally invasive procedures are generally designed with reduced profiles to facilitate insertion of the tool through a minimally invasive aperture and to prevent tissue damage from movement of the tool in a minimally invasive environment. Given the reduced profiles of suturing tools used in minimally invasive surgeries, the needle is typically introduced into the body cavity through a separate minimally invasive aperture. After the surgical needle is passed through a trocar into the body cavity, a physician generally uses visualization techniques to orient or manipulate the needle with another endoscopic tool or the suturing device until the surgical needle is placed and oriented properly within the suturing device. As this requires an additional minimally invasive aperture within the patient and increased time to introduce and orient the needle, this process can prolong the procedure, increase the likelihood of contamination and result in an increased patient recovery periods. Additionally, locating and manipulating the needle using visualization techniques can be troublesome and time-consuming, further increasing fatigue on the physician, and in some cases, resulting in loss or unintended movement of the needle.

There have been a variety of proposals for modifications to standard surgical suturing structures and methods to try to address the above disadvantages. At least some of these proposals may seek to rely on systems using specialized and/or proprietary suturing needles, which could increase costs and preclude their wide acceptance, especially in third world countries. Unfortunately, many proposals for modifying existing suturing techniques may also decrease the surgeon's control over the placement of the suture, such as by relying on an automated or indirect mechanical movement of a device to drive a suture needle into and/or through tissues. While these new proposals have in the past or may in the future gain varying degrees of acceptance in one or more surgical procedures, standard suturing techniques continue to predominate throughout surgery in general.

In light of the above, it would be desirable to provide improved suturing devices, systems, and methods. It would be generally desirable to maintain some, most, or all of the advantages of standard suturing techniques, preferably while decreasing the time required to load the needle, the strain on the surgeon, the training involved in achieving competence or time-efficiency in suturing and needle loading techniques, or the like. It would be particularly advantageous if these improvements could be provided for minimally invasive and/or open surgical procedures, optionally without requiring extensive capital investments for new equipment, without significant increases in complexity of the suturing process, or without having to resort to specialized or proprietary suturing needles and the like. Alternative needle loading structures which improve the introduction and loading of standard surgical needles into a suturing device during an endoscopic procedure without requiring additional minimally invasive apertures and which are readily adapted for a variety of different procedures and patient physiologies would also be desirable. It would be further desirable to deliver the needle along with the endoscopic suturing device through cannulae, trocars, or other minimally invasive surgical access tools and load the needle with the proper alignment in the suturing device without having to resort to visualization techniques to position and align the needle within the device.

BRIEF SUMMARY OF THE INVENTION

The present invention generally provides improved medical suturing devices, systems, and methods. Embodiments of the invention provide improved needle loading capability for suturing systems, devices and methods that maintain some or all of the advantages of standard open and/or minimally invasive suturing techniques while providing enhanced speed and ease of use. While some embodiments will find uses in a wide range of open surgical procedures, many advantageous embodiments will be particularly useful for minimally or less invasive surgeries, otolaryngology, pediatric surgeries, endoscopic surgeries (with or without trocar access), laparoscopic surgeries, and/or other procedures in which access to a suture site is limited. The present invention allows for loading of a standard surgical needle using a needle loader positionable near a distal portion of a body of a suturing device. In an exemplary embodiment, the needle loader supports the needle in a delivery position and a needle loading position. When supported in the delivery position, the needle has a delivery profile suitable for advancing through a minimally invasive aperture. When supporting in the needle loading position, the needle is aligned with one or more clamps of the suturing device to facilitate loading of the needle by grasping a portion of the needle with the one or more clamps of the suturing device. After the needle is loaded or supported by the one or more clamps, the needle loader may be removed, such as by releasing a needle loader coupled to the device body or, alternatively, by retracting a needle loader axially positionable in the device body.

In many embodiments, once the needle is advanced to the surgical site and loaded into one ore more clamps of the suturing mechanism (e.g. supported by the one or more clamps), suturing of the tissue can be performed by alternating support of the needle between at least first and second clamps of the device. Articulation motions may be transferred from a handle to a needle grasping clamp using an axial movement of an actuation shaft that is loaded in compression along an elongate axis of the device and within an outer body or sheath, although alternative embodiments may make use of actuation cables loaded in tension. Typically, the device includes two alternating clamps that both advance axially and rotate to grasp the needle, the gripping forces on the needle being substantially applied along a longitudinal axis of the device and the grasping surface being substantially parallel to the needle's plane of curvature. Gripping the needle so that the needle is stressed slightly when the clamps alternate can be advantageous as it may inhibit "walking" of the needle in the longitudinal direction that may occur as the clamps alternate holding the needle. After suturing of the target tissue is complete and release of the needle loader from the body of the device, the needle loader may be withdrawn through the minimally invasive aperture or, when slidably disposed in the body of the device, the needle loader may be retracted and concurrently withdrawn with the device.

In a first aspect, the invention provides a needle loading device for loading a standard suturing needle in a suturing device having one or more clamps. The device comprises a body having a proximal portion and a distal portion. The distal portion comprises the working portion having clamps that suture the tissues, the distal direction being toward the tissues of the patient. The proximal portion is held by the surgeon to control the device, the proximal direction being toward the surgeon. The body may include a first and second shaft that extend from the distal portion and are movable axially along the device axis and rotatably about each shaft. A first and second clamp are supported by the first and second shafts, respectively, and may be mounted at a distal end of the shaft, the shaft extending distally from the body. Each clamp comprises a proximal and distal jaw, the distal jaw being distal of the proximal jaw along an axis of the device. Movement of the first and second clamps is effected by a linkage within the body of the device. When actuated, the linkage causes movement of the clamps between a retracted displaced position and a grasping position by axially moving and rotating each shaft. When in the grasping position, each clamp grasps a portion of the needle disposed between the proximal jaw and the distal jaw along the device axis. When in the retracted position, each clamp is rotated laterally away from the needle and retracted proximally to increase clearance between the retracted clamp and the tissue and/or needle. In some embodiments, any or all of the clamps, jaws and shafts may be made of a rigid material.

In an exemplary embodiment, an endoscopic suturing needle loader device comprises a body having a proximal portion and a distal portion with a device axis extending therebetween, one or more clamps disposed near the distal portion and a needle loader releasably coupled to a needle and positionable near the distal portion. The needle loader alternates supporting the needle in a needle delivery position, wherein the needle has a delivery profile along the device axis to facilitate introduction of the needle through a minimally invasive aperture, and a needle loading position having a larger profile along the device axis, wherein the needle is aligned with a first or second clamp so as to facilitate grasping with one or more clamps of the suturing device. Preferably, the one or more clamps, preferably a first and second clamp, are operatively coupled to the device so that actuation of a clamp effects grasping of the needle with the clamp when the needle is aligned with the first clamp in the needle loading position.

In a preferred embodiment, the suturing device includes a handle at the proximal end of the body. The handle is coupled to the first and second clamps by the linkage mechanism so that an actuation of the handle alternates between: the first clamp in the grasping position while the second clamp is in the retracted position; and the second clamp in the grasping position while the first clamp is in the retracted position. Preferably in grasping the needle, the linkage axially advances the first or second clamp along an elongate axis of the device, rotates the clamp about an axis of a shaft supporting the clamp (with the clamp being offset from the shaft axis so that the clamp moves laterally toward an axis of the needle), slightly advances the clamp axially along the axis of the body of the device so as to stress the needle, and then closes the clamp on a portion of the needle. Ideally, an actuation of the handle comprises the handle moving from a first position to a second position, typically performed by a physician squeezing the handle with one hand. In some embodiments, the device may include a mechanism for effecting rotation of the needle supported with the needle loader upon actuation of the handle by a surgeon.

In an exemplary embodiment, the needle loader includes a needle holding member that supports the needle, and an elongate body pivotally coupled with the needle holding member. Preferably, a proximal portion of the elongate body couples with a distal portion of the body of the device and a distal portion of the elongate body pivotally couples with the needling holding member. The needle holding member is rotatable such that the needle may be rotated from the needle delivery position to the needle loading position. In many embodiments, when the needle loader is positioned or coupled to the distal portion of the body of the device and when the needle is supported in the needle delivery, the needle is aligned with the device axis, and when the needle is supported in the needle loading position, the needle is transverse to the device axis. Typically, a plane of curvature of the needle is aligned with the device axis, when in the needle delivery position, and the plane of curvature of the needle is transverse, preferably perpendicular to, the device axis, when the needle is supported with in the needle loading position.

In many embodiments, the needle is supported within the needle holding member in a pre-determined alignment relative the needle holding member. Typically, the needle holding member includes a needle receiving slot in one side for supporting the needle in the pre-determined alignment relative. The needle may be dimensioned so as to secure the needle in the pre-determined alignment with an interference fit or a snap-fit. The elongate member coupled with the needle holding member may optionally include a needle receiving groove in one side that supports a portion of the needle when positioned in the needle delivery position. Preferably, the needle receiving groove faces in the opposite direction as the needle receiving slot when the needle is positioned in the needle delivery position so as to secure the needle into the position and inhibit loss of the needle during delivery through the minimally invasive aperture.

In an exemplary embodiment, a proximal portion of the needle loader includes a coupling feature for coupling with a body of the device, and in some embodiment a shaft of the device. The coupling feature may include an expandable portion or a bulbous feature that snaps into or interfaces with a receiving feature of the device body or shaft. In many embodiments, the distal portion of the body of the device includes an aperture for inserting the elongate body of the needle loader and a side-hole for receiving the coupling feature (e.g. bulbous or spherical feature) of the elongate body. After the needle is loaded, the needle loader may be released by applying pressure to the coupling feature with a tool, either through the side hole or from within the device body. Release of the needle loader from the body device may effect release of the needle from needle loader, when the needle is supported with one or more clamps of the device.

In an exemplary embodiment, the needle holding member has a rotational range of motion of about 90 degrees. In such an embodiment, rotation of the needle holding member in one direction terminates in the needle delivery position and rotation of the needle holding member in the opposite direction terminates in the needle loading position.

In an alternative embodiment, the needle loader may couple with a mechanism of the body of the device, such as a rod or shaft. The mechanism may optionally include means for rotating the needle holding member of the needle loader and allow for axial movement of the needle loader relative the one or more clamps. For example, the needle loader may couple with an elongate shaft such that axial movement of the shaft retracts the needle loader after grasping of the needle with the clamp, thereby releasing the needle from the needle loader and retracting the needle loader into the body of the device.

In other embodiments, the device includes a clamp configuration such that axial advancement of one or more clamps of the device applies force to the needle or needle loader that rotates the needle from the delivery position into the needle loading position. Optionally, the one or more clamps may include a chamfered portion that nudges the needle into the needle loading position when the one or more clamps are advanced axially.

In yet another aspect, the invention provides suturing methods that include loading a needle in a suturing device. The method introducing a body of a suturing device to a surgical site through a minimally invasive aperture in a patient, introducing a needle to the surgical site by advancing a needle loader coupled to the needle through the minimally invasive aperture, moving the needle into a needle loading position, from outside the patient's body, wherein the needle is aligned with a clamp of the device, grasping the needle with the first clamp while the needle is supported by the needle loader in the needle loading position, and releasing the needle from the needle loader while the needle is supported a clamp. Typically, moving the needle includes rotating the needle, which may be effected by pushing the needle against a tissue, or applying a force to the needle or needle loader with a tool or a mechanism of the device.

In an exemplary embodiment, the method includes removing the needle loader from close proximity with the clamps after grasping of the needle with one or more clamps of the device. Removing of the needle loader may be effected by releasing the needle loader, when releasably couple with a distal portion of the body of the device, or by retraction of the needle loader when coupled with a rod or shaft. Releasing of the needle loader may be effected by applying a force on a coupling feature disposed on a proximal portion of the needle with a tool or mechanism of the device. The method may further include retrieving and removing the needle loader after suturing has been completed and the body of the device withdrawn through the minimally invasive aperture.

In another aspect, the method includes selecting a standard surgical needle for suturing with the device, coupling the needle in the needle loader, coupling the needle loader to the body or a mechanism of the device and loading the needle using any of the methods described herein. In alternative embodiments, the method may include selecting a standard surgical needle pre-coupled with the needle loader, and coupling the needle loader with the device, or a mechanism of the device, to facilitate loading of the needle and suturing with the selected surgical needle.

For a fuller understanding of the nature and advantages of embodiments of the present invention, reference should be made to the ensuing detailed description and accompanying drawings. Other aspects, objects and advantages of the invention will be apparent from the drawings and detailed description that follows. However, the scope of the invention will be fully apparent from the recitations of the claims.

DETAILED DESCRIPTION OF THE INVENTION

The present invention provides improved medical devices, systems, and methods for applying of surgical sutures. Properly realized, the invention facilitates needle loading in suturing devices for use in endoscopic and/or open techniques for suturing tissues, which can significantly increase the speed and enhance the simplicity of suture application, allowing for improved results and minimizing patient recovery periods.

This invention should find extensive use in tissue suturing during surgical operations on both humans and animals, and is particularly advantageous in endoscopic procedures (for example, during laparoscopy), and in operations that involve limited access and in other surgical areas where tissue joining is desired. The devices and related techniques described here can be used, for example, to suture different layers of anatomical tissues, including (but not limited to) various organs (among them, the intestines and the uterus), and so forth. A wide range of blood vessels, including veins and arteries, can also be connected using the techniques described in this document in order to form anastamoses and so on. In addition to increasing the speed and/or facilitating the creation of a surgical suture, devices based on the subject invention reduce the likelihood of contamination by minimizing contact with the suturing needle during loading as well as reducing the number of minimally invasive apertures needed to perform a suturing procedure. A version of the invention can be used in any number of suturing devices, including but not limited to any of the embodiments disclosed in U.S. patent application Ser. No. 13/168,426 filed Jun. 24, 2011 and titled "Endoscopic Suturing Device, System, and Method," and U.S. patent application Ser. No. 11/532,032 filed Sep. 14, 2006 and titled "Suturing Device, System, and Method," or in automated systems, for example, in robotic systems.

The devices described here provide for standard sterilization techniques used for surgical instruments, which implies reuse. In many embodiments, the needle loader is detachable and can be sterilized for re-use. Sterilization can be accomplished using an autoclave, as well as chemical sterilization techniques, irradiation, etc., since most or all of the device parts can optionally be made from materials suitable for repeated sterilization (such as stainless steel, other metals, alloys, etc.). Alternatively, the needle loader may be disposable and discarded after a single use.

Suturing devices based on the subject invention make it possible to employ standard suture materials with standard needles commonly used in surgery, for example, needles with flat gripping surfaces, as well as needles with a round, triangular, or other cross-sections. Typically, the surgical needle will have a radius of curvature that often includes a base portion and a sharp penetrating portion.

Figure 1:
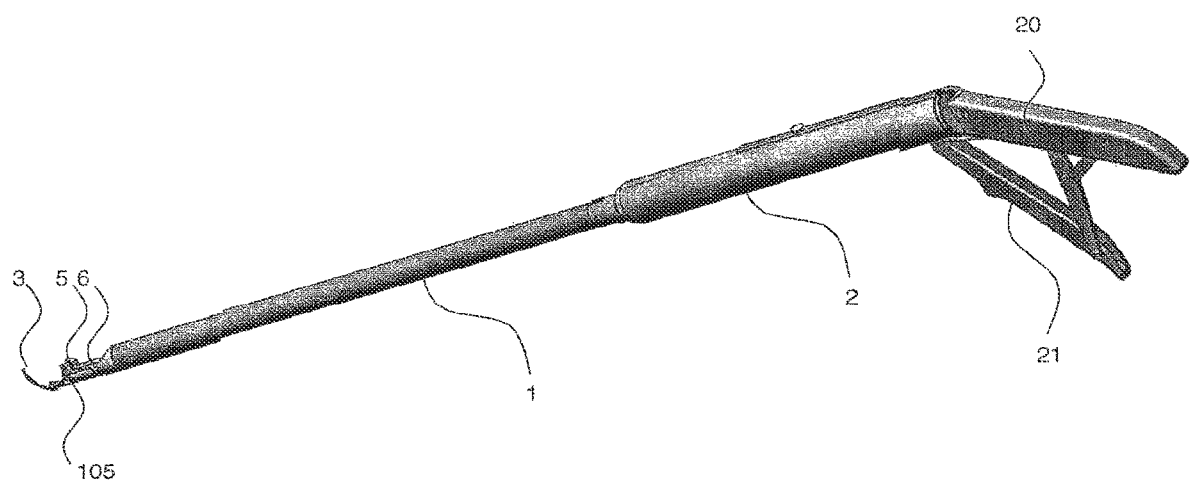
FIG. 1 shows an exemplary suturing needle loading device.

Referring now to FIG. 1, an exemplary embodiment of the suturing device includes a body having a distal portion 1 and a proximal portion 2 and device axis extending therebetween. The distal portion 1 comprises two clamps 5 and 6 for alternating grasping of a surgical needle 3, and a needle loader 105 that alternates supporting the needle between in a delivery position and a needle loading position. When in the needle delivery position, the needle is oriented so as to reduce the profile of the needle into the delivery profile to facilitate advancement of the needle 3 in an endoscopic procedure (e.g. aligned with the device axis). When in the needle loading position, the needle 3 is aligned or oriented so as to facilitate grasping with either of clamps 5 or 6. In an exemplary embodiment, the needle 3 rotates between the delivery position and the needle loading position (e.g. substantially perpendicular to the device axis) while supported with the needle loader. The proximal portion 2 comprises a handle 20 by which the physician holds the suturing device and a movable handle 21 by which the surgeon actuates the clamps 5 and 6 of the device to suture a tissue, particularly during an endoscopic procedure. In an exemplary embodiment, the needle loader 105 is coupled with the distal portion 1 before a procedure and the needle 3 is positioned, such as with a tool, so that the needle 3 is aligned in the delivery position. After advancement of the needle loader 105 supporting the needle 3 in the delivery position, a physician may nudge the needle 3 against tissue, or with a tool, to rotate the needle into the needle loading position. Once positioned in the needle loading position, the needle 3 may be grasped by either of clamps 5 or 6 upon actuation of the moveable handle 21 by the surgeon. Alternatively, the needle loader 105 may include an actuation mechanism, such as a rod, shaft or pullwire, coupled with a rotatable portion of the needle loader 105 to effect rotation, so that the physician may effect rotation of the needle 3 from the delivery position to the needle loading position from the proximal portion 2 of the device.

Typically, during advancement of an endoscopic suturing needle loading device into a body cavity of the patient, the surgical needle 3 is supported with the needle loader 105 in the needle delivery position such that a plane of curvature of the needle is substantially parallel with a longitudinal axis of the needle loader. After the suturing device is advanced to the target tissue to be sutured, needle loader 105 positions the needle to a needle loading position to be grasped by either of clamps 5 or 6. Positioning of the needle 3 into the needle loading position may include axial advancement of the needle loader and/or rotation of the needle 3 relative to the longitudinal axis of the needle loader. Preferably, positioning the needle 3 in the needle loading position includes rotating the needle 3 such that the plane of curvature of the needle 3 is substantially perpendicular to the longitudinal axis of needle loader 105. After the needle 3 is positioned in the needle loading position by the needle loader 105, either of clamps 5 or 6 are actuated to grasp the needle 3, thereby transferring supporting of the needle from the needle loader 105 to the grasping clamp. Release of the needle loader 105 from the body of the device may be facilitated by axial movement of the needle loader 105, once needle 3 is grasped in either of clamp 5 or 6.

Once the needle 3 is supported within clamps 5 or 6, repeated actuation of the clamps alternates grasping of the needle between clamps 5 and 6 to facilitate suturing at the target tissue. To increase the clearance near the needle during suturing, needle loader 105 may be released from the suturing device, further advanced, or retracted along its longitudinal axis.

In some embodiments, the needle loader 105 may be operatively coupled with a mechanism of the device such that a surgeon may actuate the needle loader 105 from a proximal portion of the device, such as by pressing a handle of the device. Actuation of needle loader 105 may include re-orienting or rotating the needle relative to an axis the needle loader so as to align the surgical needle 3 into the deliver position. Actuation of the needle loader 105 may further include advancement of the needle loader 105 along its longitudinal axis to axially position the needle 3 into a position suitable for grasping with one or more clamps of the device, and may further include retraction of the needle loader 105 along its longitudinal axis after loading of the needle 3 into either of clamps 5 or 6. Actuation of needle loader 105 may be performed by the physician with movable handle 21 or with one or more additional mechanisms disposed near proximal portion 2.

Figure 2A:
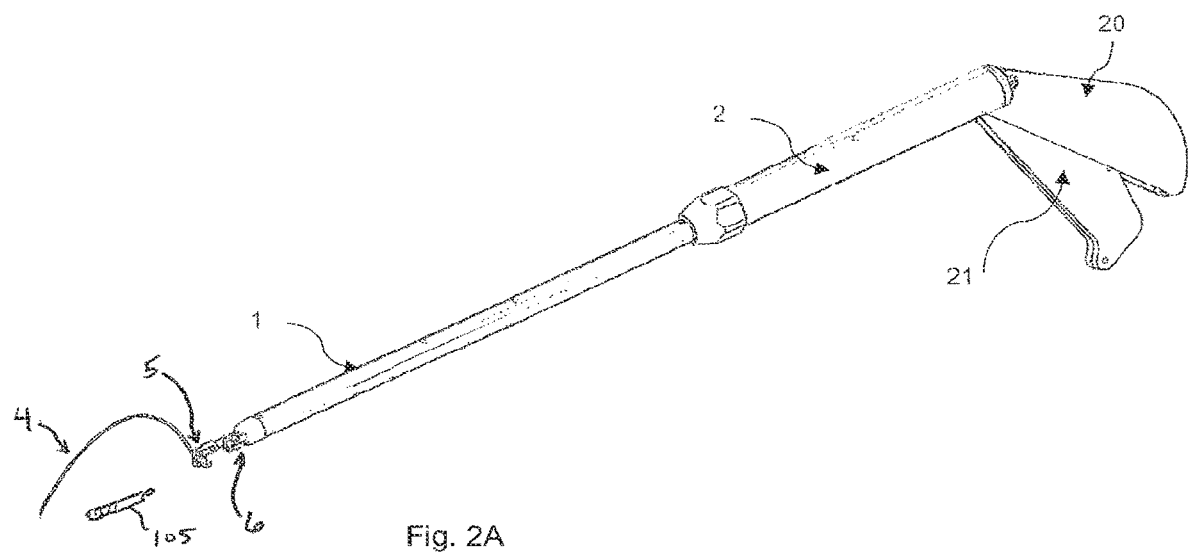
FIGS. 2A-2B shows a detached needle loader and a suturing device having a detachable distal portion, in accordance with many embodiments.
Figure 2B:
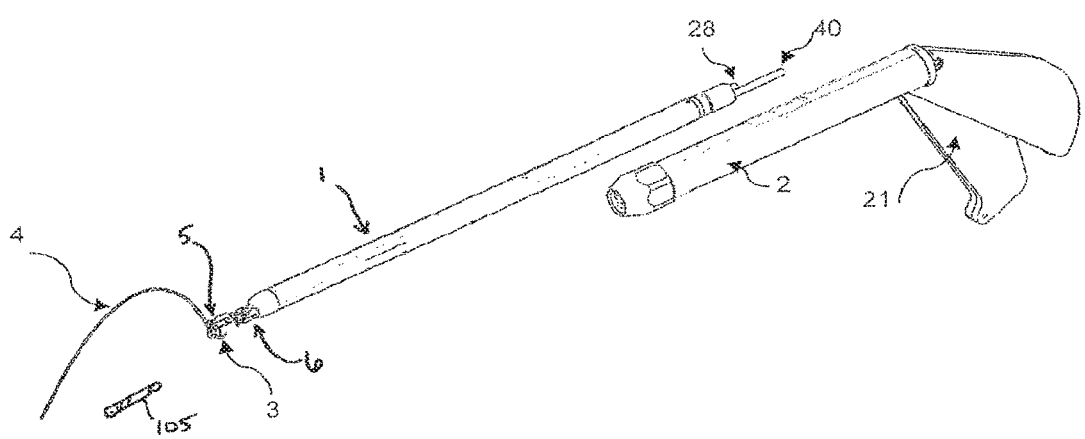

FIGS. 2A and 2B illustrate another embodiment of the suturing device that includes a body having a distal portion 1 and a proximal portion 2, after the needle 3 has been loaded into clamp 5 and the needle loader 105 has been released from the body of the device (shown detached in FIGS. 2A and 2B). The distal and proximal portions of the device body can be fabricated as an integrated whole or as separate units that can be joined before surgery by a quick-disconnect coupling, as shown in FIG. 2B, for example. The detachable distal portion 1 may be disposable or may have several modifications for different applications. The distal portion 1 comprises two compression rods 28, 40 coupled to two clamps 5 and 6. When the assembled device is repeatedly actuated, the clamps may alternate holding a surgical needle 3 so that a physician can suture a tissue with thread 4. The proximal portion 2 comprises a handle 20 by which the physician holds the suturing device and a movable handle 21 by which the surgeon actuates clamps 5 and 6 of the device to suture a tissue, particularly during an endoscopic procedure.

The distal portion 1 of the suturing device body typically comprises a long, narrow body or working part with a round cross-section. The application for a device determines the dimensions of distal portion 1. For instance, the distal portion 1 of a device for endoscopic procedures can consist of a long narrow working part, having a cross-section that can be inserted through a trocar, and a length that ensures suture application at the desired depth. The proximal portion 2 of the body includes a handle 20 by which a physician can hold the suturing device and a movable handle 21 by which the physician can actuate the suturing device.

In some embodiments, the movable handle may be used to actuate both the needle loader 105 and the clamps 5 and 6. A mechanism, such as a lever or button, on proximal portion 2 may be used to alternate operative coupling of the handle actuation mechanism with needle loader 105 and clamps 5 or 6. For example, when the mechanism is coupled with needle loader 105, actuation of the handle 20 by squeezing the movable handle 21 would move the mechanism coupled with the needle loader 105 causing needle 3 to rotate into the needle loading position. Alternating the mechanism to couple with the clamps, moving the handle 21 would cause clamp 5 or 6 to grasp the needle held by the needle loader 105 in the needle loading position. Once grasped with clamps 5 or 6, the needle loader 105 can be released or retracted into distal portion 1 by retraction of a rod or shaft coupled to needle loader 105.

Figure 3:
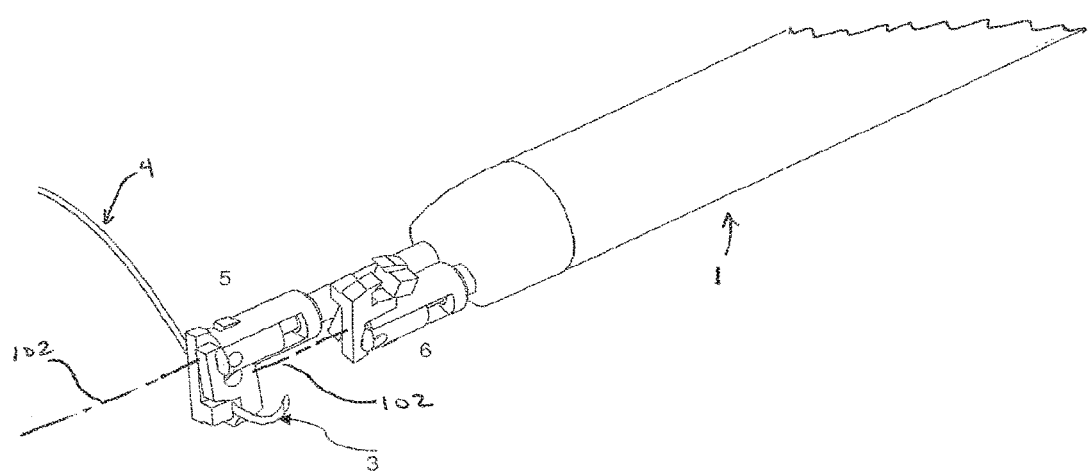
FIG. 3 shows two clamps of an exemplary suturing device after release of the needle loader, one clamp in an extreme distal position grasping a needle and the other clamp retracted into an extreme proximal position.
Figure 4:
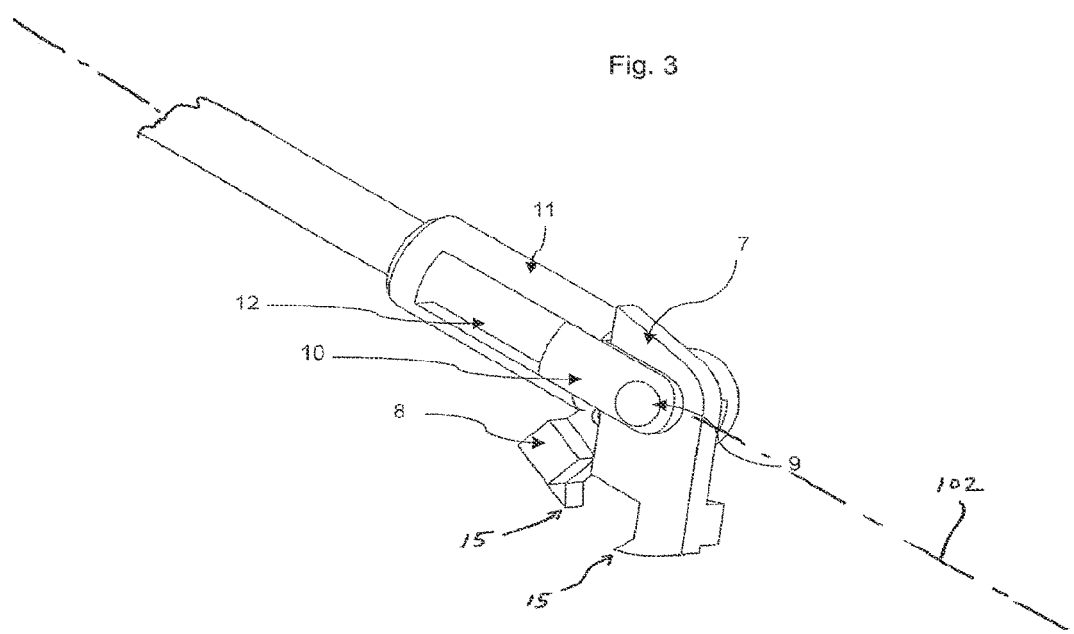
FIG. 4 shows a clamp having two jaws for grasping the needle.

The needle loader 105 and clamps of the suturing device may be used with a standard surgical needle 3, usually curved in shape, to the base of which a suturing thread 4 is attached. The needle's dimensions can be selected in accordance with the type of tissues being joined. The two clamps, clamps 5 and 6, shown in FIG. 3 for example, are located at or near the distal end of distal portion 1. In the embodiment of FIG. 3, clamp 5 grips the needle near a base of the needle where thread 4 is attached, while the other clamp 6 sits open in a retracted position. When actuated, clamps 5 and 6 alternate holding the needle. When clamp 6 grips the needle 4 along an insertion portion near the sharp end, clamp 5 retracts to an extreme proximal. Ideally, clamps 5 and 6 are identical, allowing a needle to be clamped for suturing both from right to left, as shown in FIG. 3, and from left to right, if the surgeon held the handle in the left hand, for example.

Figure 5:
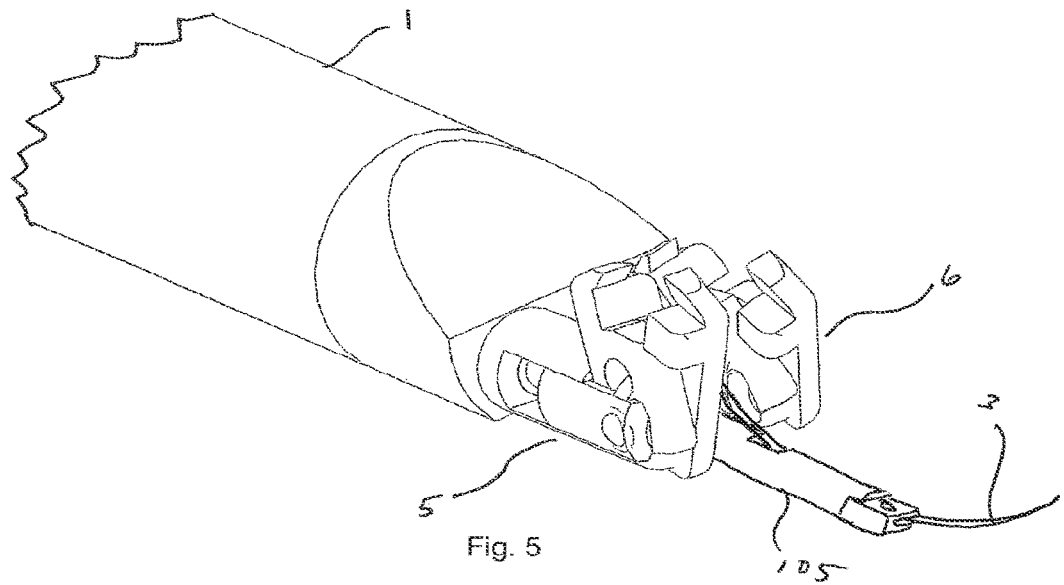
FIG. 5 shows an exemplary suturing device with both clamps in the extreme proximal position and coupled with a needle loader holding a needle in the delivery position.
Figure 6:
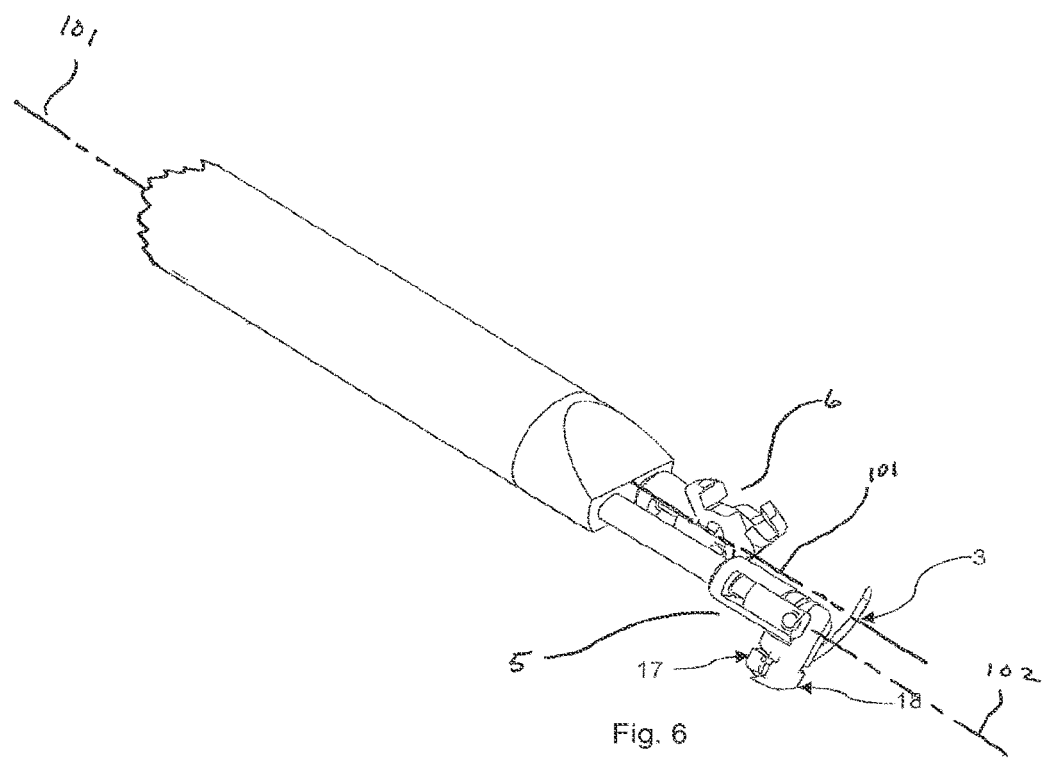
FIG. 6 shows an exemplary suturing device after loading of the needle and release of the needle loader, one clamp shown in an extreme distal position grasping a needle and the other clamp shown retracted in an extreme proximal position.

In the initial state, for example, the clamps are in the proximal position as the device passes through a trocar, the jaws being turned as shown in FIG. 5, and the needle 3 held in the delivery position by needle loader 105 coupled to distal portion 1. Here, the surgeon holds the device by handle 20 (FIG. 1). After introduction of the needle and device to the target tissue to be sutured, the physician may move the needle into the needle loading position (e.g. by pushing the needle against a tissue or a tool causing it to rotate into position). Once the needle is in the needle loading position, the surgeon my press movable handle 21 to grasp the needle with clamp 5 or 6. Once the needle is supported with clamp 5 or 6, the surgeon may release the needle by de-coupling the needle loader 105 from the device body or by retracting the needle loader 105. Removal of the needle loader 105 from proximity of the clamps allows the surgeon adequate clearance to suture the target tissue by alternating supporting the needle 3 with clamps 5 and 6. Each time the movable handle 21 is pressed, one of the clamps advances to the extreme distal position and turns around the axis 102 of the clamp's shaft. Jaws 17 and 18 then close and grip needle 3, as in FIG. 6 for example. The surgeon may then suture the tissue by pushing the needle 3 through the tissue by moving or rotating the body of the device about an axis 101 of the device.

Figure 7:
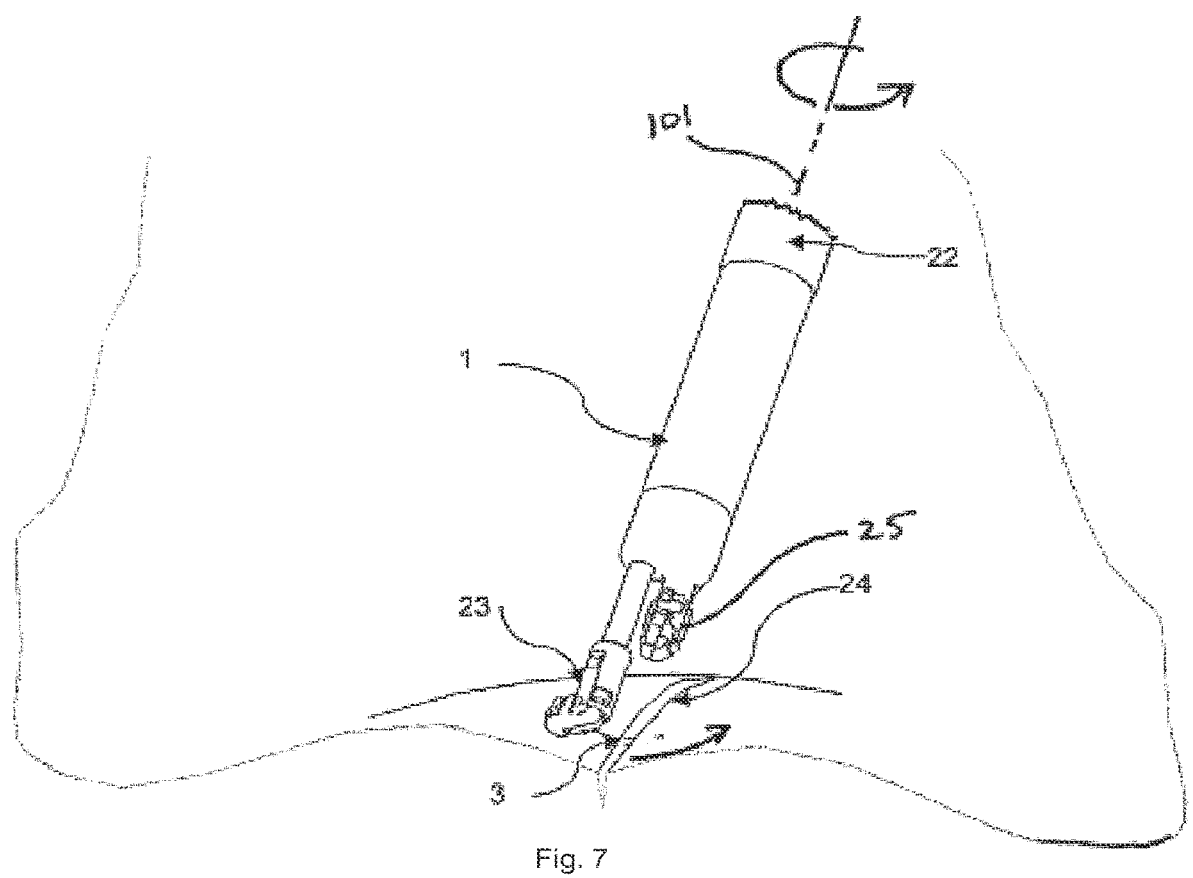
FIG. 7 shows an exemplary suturing device after loading of the needle, with one clamp shown grasping the base of the needle, the rotational movement of the device driving the sharp end of the needle through the tissue.

The suture application process is depicted in FIG. 7, where the working part of distal portion 1 is shown inserted through a trocar 22, while clamp 23 holds needle 3 in place. Rotating the device around the axis of the device 101, the surgeon pierces the tissue with the needle near the incision and draws needle 3 through the tissue in order to complete the suture stitch. When movable handle 21 is pressed again, the second clamp 25 advances to the extreme distal position and turns around the shaft. Jaws 17 and 18 of the second clamp 25 close and grip needle 3 near its sharp end. Then, the first clamp 23 opens its jaws 17 and 18, freeing the needle, then turns around its shaft and moves into its initial state. Thus, the needle is engaged and the device now holds the needle near its sharp end, allowing the surgeon to pass the base portion of the needle and the thread 4 through the puncture. Subsequently pressing the movable handle results in clamp 23 gripping the needle at its base and the opening of clamp 25. Thus, by successively pressing movable handle 21, the surgeon engages the needle with alternating clamps and has the ability to apply a suture stitch without using additional instruments. This not only leaves the surgeon's other hand free, but also considerably expedites the suture application process.

A linkage mechanism, the first part of which is housed in distal portion 1 (FIG. 1) and the other part of which is housed in proximal portion 2, is responsible for the functioning of the device. Here, the first part of this mechanism supports the clamp turning and needle gripping sequence, while its second part ensures clamp changeover and the transmission of needle gripping force from movable handle 21 to the clamps.

In the preferred embodiment, pressing the handle 21 (FIG. 1) one time causes the mechanism to move rod 28 in the distal direction and lock in the extreme position while at the time of its locking, a second rod, 40, is released and returns to the initial proximal position under the influence of a spring. When handle 21 is pressed again, rod 40 moves and locks in the extreme distal position, while rod 28 is released and returns to the initial proximal position. This functionality is realized by the linkage mechanism housed within proximal portion 2.

Figure 8:
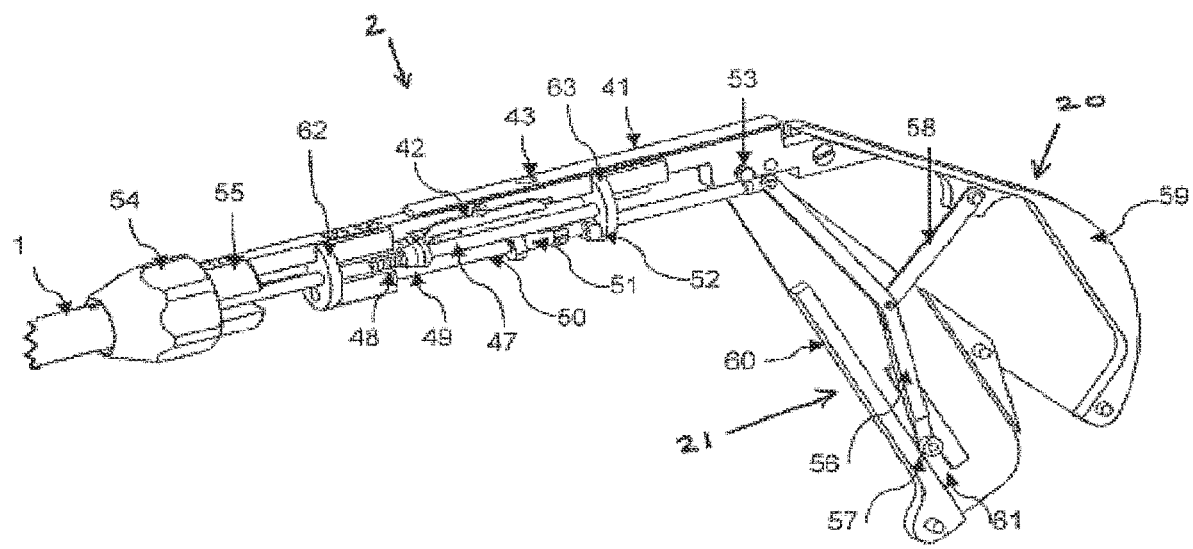
FIG. 8 shows individual components of the linkage within the proximal portion of the suturing device that effect movement of the clamps.

An exemplary linkage mechanism housed in proximal portion 2 is shown in FIG. 8. Proximal portion 2 consists of a frame 41 that is rigidly connected to a grip 59, and to the shaft 53 of which a movable handle 60 is attached. Frame 41 has two plates 62 and 63 each of which has three holes. Rods 44 and 47, with springs 45 and 48 and conical bushings 46 and 49 installed thereon, are inserted into two of the holes, while a rod 50, having a rotor 51 installed thereon, is inserted into the third hole. The end of this rod is pivotally connected to a lever 56, on the other end of which a roller 57 is installed. In its midsection, lever 56 is pivotally connected to one end of a lever 58, the other end of which is pivotally connected to grip 59. An assembly for securing distal working part 1, for example, in the form of a collet 55, with a nut 54, is installed on the distal end of frame 41. A locking device 42, with a release button 43, is installed on the shaft in the midsection of frame 41. In the initial position, handle 60 is rotated away from grip 59, and lever 56 is in a position where rod 50 is shifted into the extreme proximal position. Roller 57 of lever 56 is able to move within the confines of slotted recess 61 (FIG. 8).

The operation of the mechanism is now described with rods 44 and 47 positioned in the extreme proximal position. When handle 60 is pressed, lever 56 rotates around the shaft of its pivotal connection to lever 58. An end of lever 56 bears on rod 50, causing it to move in the distal direction, while roller 57 on the other end of lever 56 moves within slotted recess 61. Rod 50 sets rotor 51 into motion in the distal direction, whereupon the latter's projection in turn pushes one of the conical bushings. For example, bushing 49, together with rod 50, bears on rod 40 (FIG. 17) of distal working portion 1 making the appropriate clamp advance and grip the needle. When handle 60 is in the extreme depressed position, bushing 49 compresses spring 48, providing the requisite needle gripping force, and locking device 42 fixes bushing 49 in this position. Handle 60 can then be released, and returns to its initial open position. At this point, the needle is still gripped and the surgeon can use the needle to penetrate tissue next to the incision. When handle 60 is released, rod 50, together with rotor 51, moves in the proximal direction under the influence of lever 56. As rotor 51 moves in the proximal direction, the extreme proximal position rotates around its shaft 90 degrees under the influence of oblique projections 64 and 63. Thus, when handle 60 is subsequently pressed, rotor 51 sets the second conical bushing 46 into motion, which in turn makes the second clamp advance forward and grip the needle. Locking device 42 fixes the bushing in the extreme distal position and bushing 49 is simultaneously released, at which time the first clamp releases the needle and returns to the initial position under the influence of spring 27, which is located in distal portion 1. The surgeon can then extract the needle from the tissue, drawing the thread through the puncture and completing the stitch. When suturing is complete, the needle can be released and removed from the patient. This is accomplished by pressing button 43, which causes lock 42 to rotate and release both clamps, thereby releasing the needle to facilitate removal.

Figure 9:
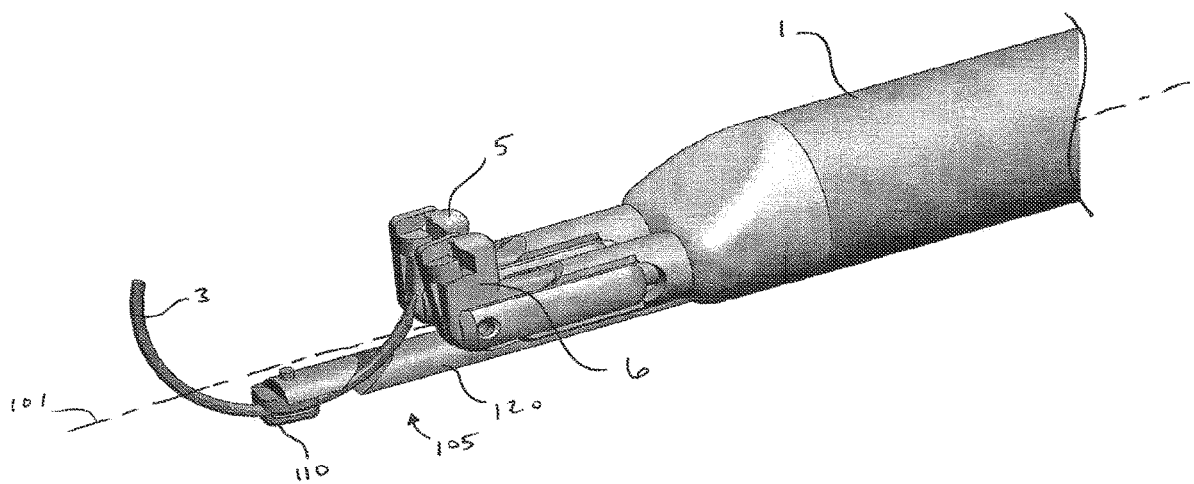
FIG. 9 shows an exemplary needle loader coupled with a suturing device.
Figure 15:
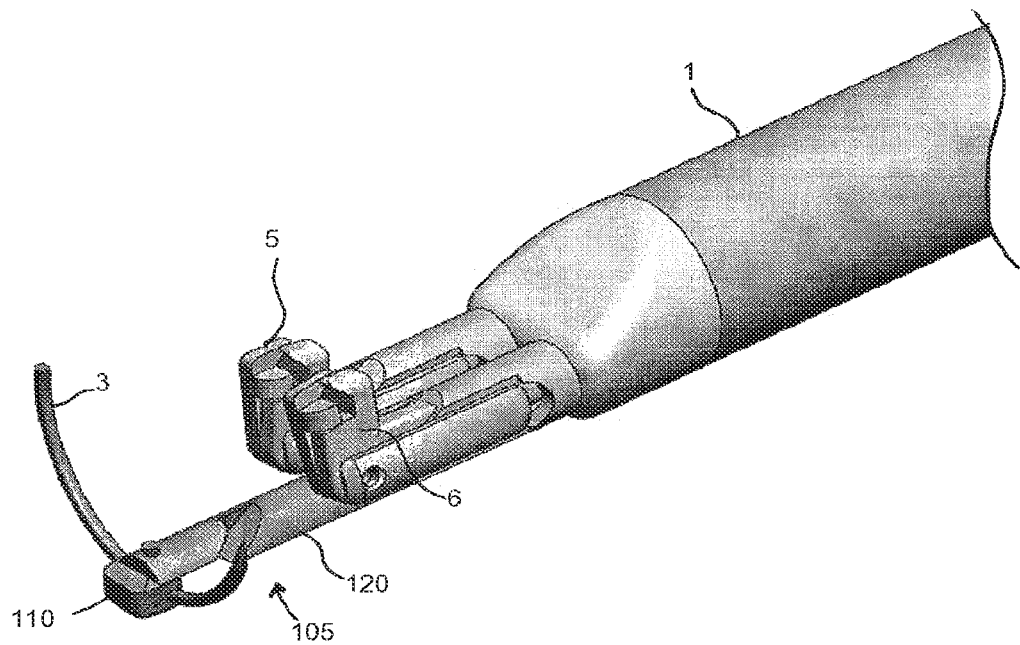
FIG. 15 shows a detail view of a suturing device coupled with an exemplary needle loader supporting a needle having been rotated into the needle loading position.

Referring now to FIG. 9, an exemplary embodiment of a needle loader 105 is shown incorporated into a suturing device. The needle loader 105 couples to the device body's distal portion 1 near clamps 5 and 6. In this embodiment, needle loader 105 includes an elongate body 120 and a rotatable needle holding member 110. The proximal end of elongate body 120 couples to the device body's distal portion 1, while the distal end of elongate body 120 pivotally couples to the rotatable needle holding member 110, which, in turn, releasably couples needle 3, selectable from any number of needles. The needle holder 110 is configured to hold the curved needle in a pre-determined alignment relative to the needle holder 110, typically with a slot or groove in one side of needle holding member 110. Preferably, needle holding member 110 rotates between at least two positions, a needle delivery position and a needle loading position. In the needle delivery position (as shown in FIG. 9), the needle holding member 110 is positioned such that the needle 3 held therein is aligned with a longitudinal axis of the elongate member 120 and/or a longitudinal axis 101 of the device body. Typically, when aligned in the needle delivery position, a plane of curvature of the needle is substantially aligned with or parallel to the longitudinal axis of the elongate member 120 or the device body's distal portion 1. The needle 3 is positioned in needle holding member 110 so as to have a delivery profile, typically a reduced profile along the device axis along which it is advanced, to facilitate advancement of the needle 3 with the device. In the needle loading position, the needle holding member 110 is rotated relative to the elongate body 120 such that the needle is transverse, preferably perpendicular, to the longitudinal axis of the elongate body 120 or the device body's distal portion 1 (as shown in FIG. 15) so as to facilitate grasping of the needle 3 with one or more clamps of the device.

Figure 10A:
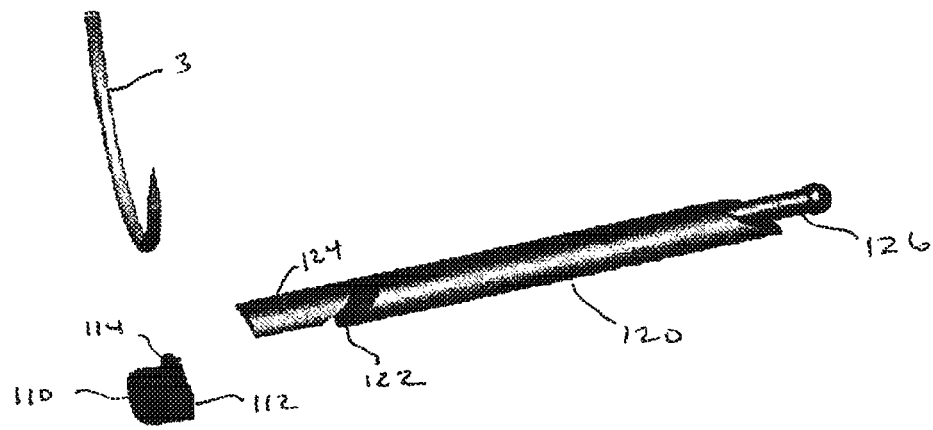
FIGS. 10A-10C show detail views of an exemplary needle loader attachment.
Figure 10B:
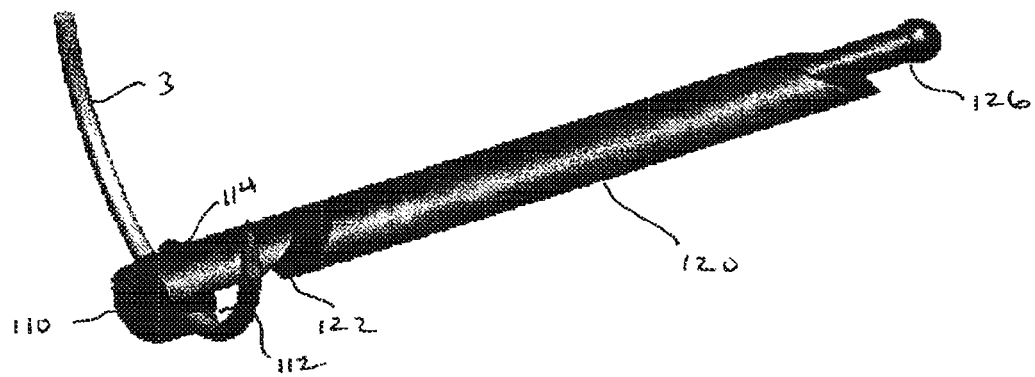
Figure 10C:
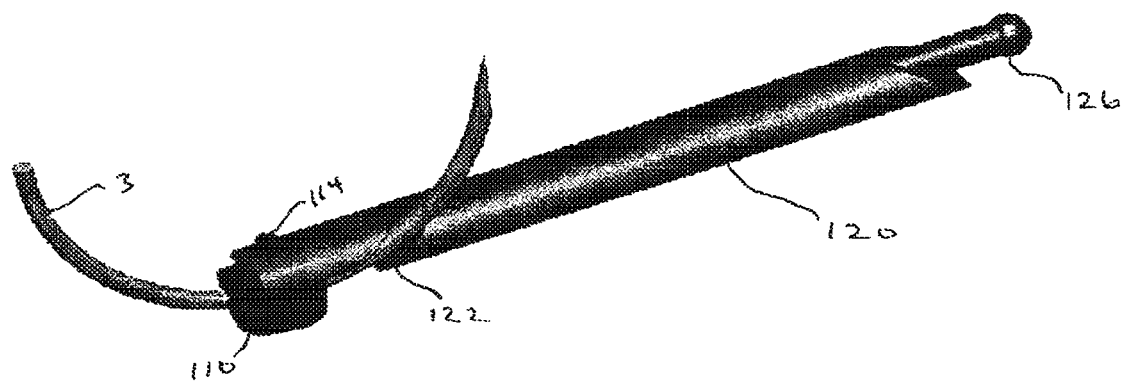

FIGS. 10A-10C show various detail drawings of an exemplary needle loader 105. FIG. 10A shows an exploded view of needle loader 105, which includes elongate body 120 and rotatable needle holding member 110, and the associated curved surgical needle 3 to be supported in needle holding member 110. In this embodiment, needle holding member 110 includes a needle holder slot 112 in one side of needle holding member 110 for receiving and holding the needle in a pre-determined alignment relative to the needle holding member 110. Typically, the slot 112 is dimensioned so that the needle 3 is held within the needle holding member 110 by an interference fit or snap-fit. The rotatable needle holding member 110 includes a pin or axel 114 that fits into a receiving hole 124 of the elongate body so as to pivotally couple the needle holding member 110 with the elongate body 120. The needle holding member 110 may be rotated relative the elongate body 120 between a delivery position (as shown in FIG. 10C) and a needle loading position (as shown in FIG. 10B). Optionally, the elongate body may further include a needle receiving notch or groove 122 for receiving the needle when the positioned by the needle holding member 110 in the needle delivery position (as shown in FIG. 10C). The receiving notch 122 allows for the delivery profile of the needle 3 and may further support the needle 3 when in the delivery position to inhibit loss of the needle 3 during delivery. The elongate body further includes coupling member 126 at its proximal end for coupling with a distal portion of the device body. The coupling member 126 may include a bulbous end for snap-fitting into the device body's distal portion, or alternatively, a wedge shaped shaft or feature that couples to the device body by an interference fit. In an alternative embodiment, the coupling member 126 may couple with a shaft or rod in the distal portion of the device to facilitate axial advancement and/or retraction of the needle loader 105 from a proximal portion of the device.

FIG. 10B shows a detail view of the needle loader 105 when positioned in the needle loading position, the needle holding member 110 having been rotated along its axel 114 so that the needle 3 held within is positioned transverse to a longitudinal axis of the elongate body 120, preferably a plane of curvature of the needle 3 is perpendicular to the device axis or axis of the elongate body. In many embodiments, the longitudinal axis of the elongate body 120 is substantially aligned with a longitudinal axis of the device body. Preferably, the needle holder slot 112 faces in the proximal direction along the axis of the elongate body 120 in the needle loading position so that releasing the needle loader 105 or moving the needle loader 105 distally would release the needle 3 when supported within one or more clamps of the suturing device. Alternatively, the needle loader 105 may be configured so that the needle holder slot 112 faces distally in the needle loading position so that axial retraction of the needle loader 105 would release the needle 3 when supported with one or more clamps of the suturing device.

FIG. 10C shows a detail view of the needle loader 105 when positioned in the needle delivery position, the needle holding member 110 having been rotated along its axel 114 so that the needle 3 is aligned with a longitudinal axis of the elongate body. In many embodiments, when the needle loader 105 positioned in the needle delivery position, a plane of curvature of the needle 3 is aligned with a longitudinal axis of the elongate member, and the needle 3 is positioned within needle holding member 110 to minimize the delivery profile of the needle 3. When in the needle delivery position, the needle 3 is received within the needle receiving groove 122 of the elongate member, which ensures proper alignment of the needle 3. Preferably, the needle holder slot 112 faces in the opposite direction as the needle receiving groove 122 of the elongate body 120 to hold secure the needle 3 within the needle loader 105, thereby preventing inadvertent loss of the needle during delivery. The needle receiving groove 122 further ensures proper alignment of the needle 3 for delivery, since rotation of the needle 3 towards the needle receiving groove terminates in the needle delivery position as the needle 3 contacts the needle receiving groove 122. For example, a should the needle holder 105 begin to inadvertently rotate out of the delivery position during delivery, a physician could nudge an end of the needle against a tissue or tool to rotate the needle holder 105 in the opposite direction until contact of the needle receiving groove 122 against the needle 3 ensures the needle holding member 110 and associated needle 3 return to the delivery position.

Figure 11A:
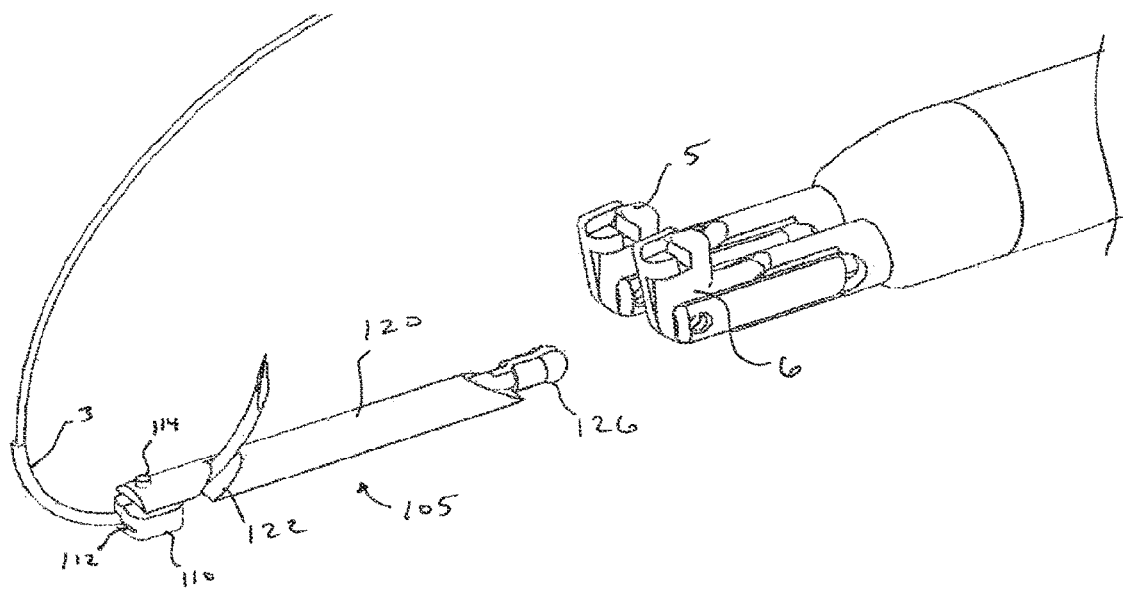
FIGS. 11A-11B show an exemplary needle loader coupled with a needle aligned for coupling with a suturing device.
Figure 11B:
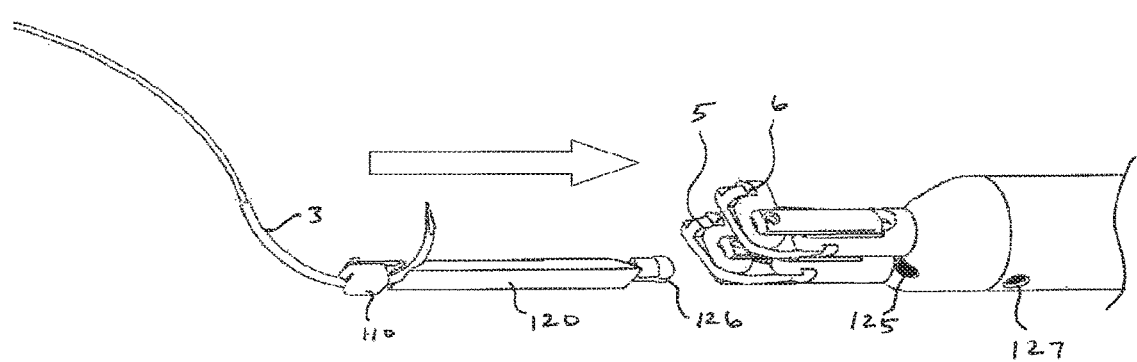
Figure 12A:
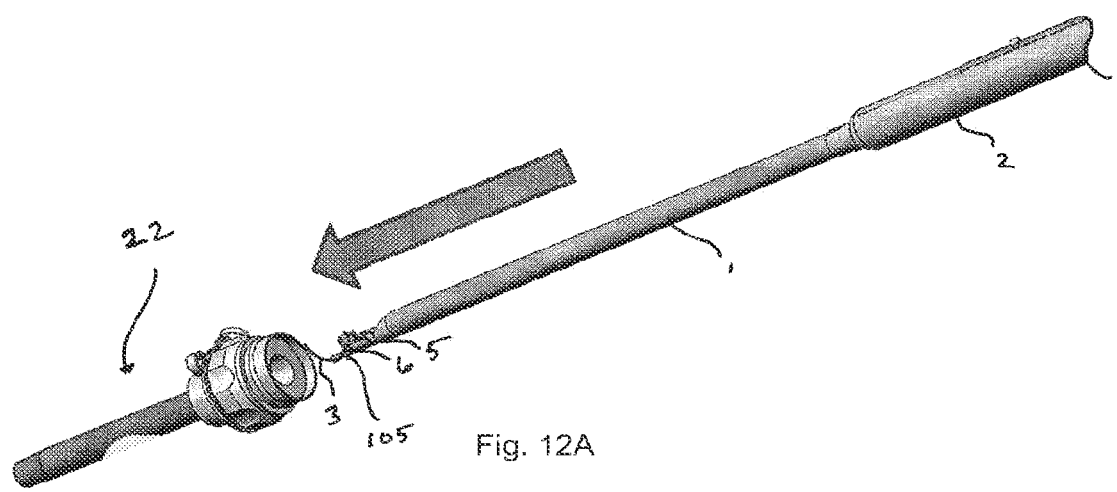
FIGS. 12A-12B show an exemplary suturing device with need loader being advanced through a trocar, the needle supported by the needle loader in a delivery position.

FIGS. 11A and 11B show the needle loader 105 before coupling with the distal portion 1 of the device body in preparation for delivery of an exemplary device through a minimally invasive aperture. The physician may select a standard, off-the-shelf curved surgical needle 3 and position the needle 3 into the needle loader 105 in the delivery position (as shown in FIG. 10C). The needle loader 105 may then be releasably coupled with the distal portion 1 of the device body by inserting the elongate body 120 through a receiving aperture 125 of distal portion 1 until the coupling member 126 fits or expands into side hole 127, such as in a snap-fit coupling. The proximal portion of elongate body 120 may be shaped so to maintain a particular alignment and orientation of the needle loader 105 relative the body of the device, as shown in FIG. 12A. Once the needle is advanced through the trocar with the device and loaded onto clamps 5 and 6, the needle loader 105 may be released by placing tension on the needle loader 105 or by pressing on the couple member through side hole 127 with a tool. Alternatively, needle loader 105 may be released by moving a rod from a proximal portion of the device to push the needle loader 105 distally, thereby releasing the needle loader 105 from the device body and associated needle 3.

Figure 12B:
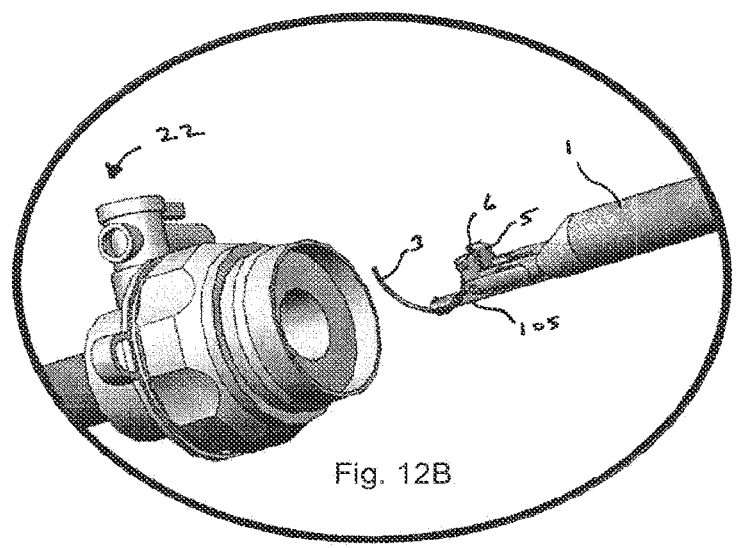

FIGS. 12A and 12B show an exemplary suturing device, as in the above described embodiments, being advanced through a trocar 22 for delivery to a target tissue site through a minimally invasive aperture of a patient. The needle loader 105 is positioned in the delivery position, as described above, such that the needle 3 held therein has a reduced profile to facilitate delivery of the needle 3 and device through the trocar 22, as shown in the detail of FIG. 12B.

Figure 13:
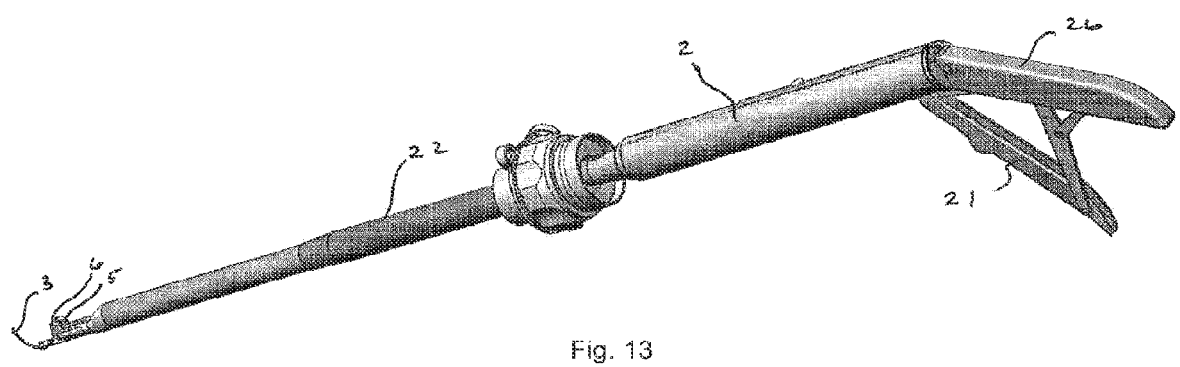
FIG. 13 shows an exemplary needle loading suturing device passed through the trocar.
Figure 14:
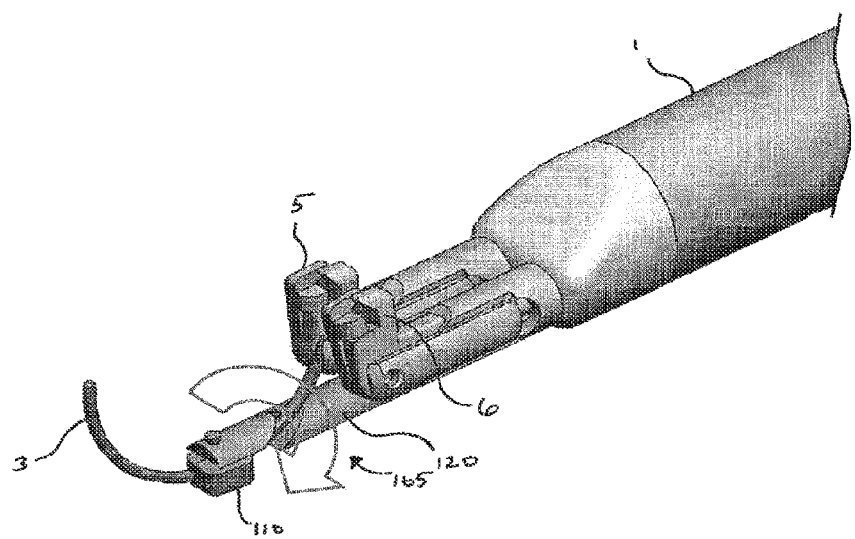
FIG. 14 shows a suturing device coupled with an exemplary needle loader supporting a needle in the delivery position before rotation into the needle loading position.

FIG. 13 shows the device of FIG. 12A after advancement through trocar 22, the needle loader 105 still positioned in the delivery position. The proximal portion 2 of the device may be used to maneuver the device until the needle 3 and clamps 5 and 6 are positioned at the target tissue site. Once positioned, the physician may move the needle loader 105 from the delivery position to the needle loading position to facilitate grasping of the needle 3 with clamps 5 and 6 and suturing of the target tissue, such as by rotating the needle 3 and needle holding member 110 in the direction of the arrow in FIG. 14. The needle holding member 110 may be rotated by manipulation of the proximal portion of the device or by actuation of a mechanism to effect rotational movement. By moving the proximal portion 2 of the device body, the physician may push the distal most portion of the needle 3 against a tissue or use a tool to rotate the needle holding member 110 relative the elongate body 120 until positioned in the needle loading position. Preferably, the needle loading position is the terminal position in rotating the needle holder 105 in one rotational direction, and the needle delivery position is the terminal position when rotating the needle holder 105 in the opposite rotational direction. Alternatively, the grasping action of one or more clamps of the device, effected by actuation of the handle 20, may act to push the needle, thereby rotating needle from delivery position to needle loading position.

Figure 16:
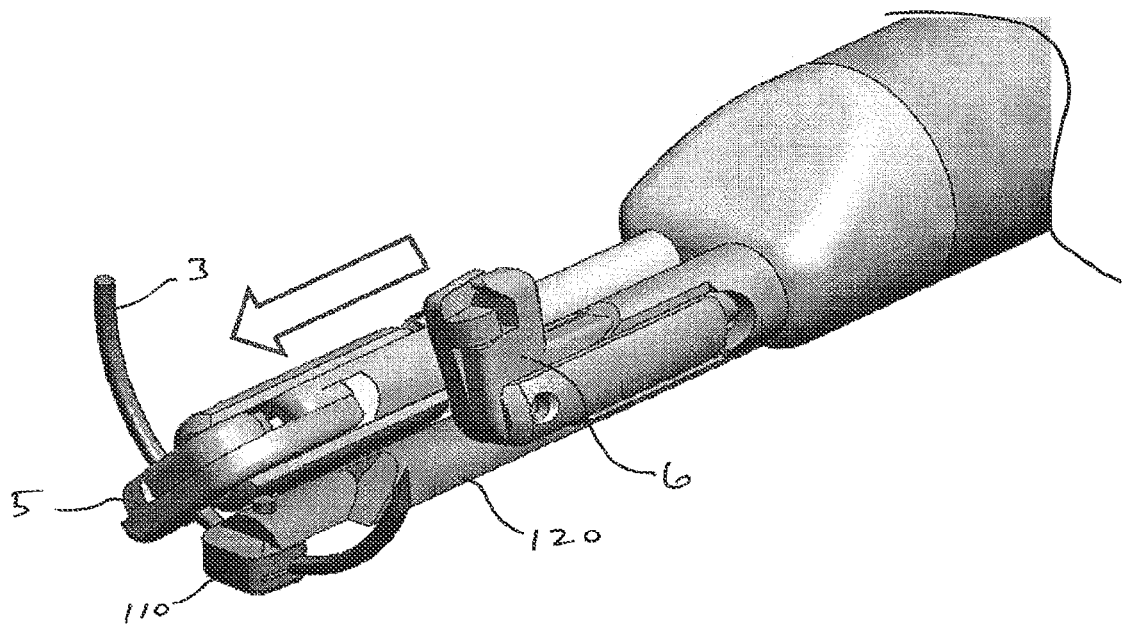
FIG. 16 shows a detail view of a clamp of the suturing device grasping a needle supported in an exemplary needle loader in the needle loading position.
Figure 17:
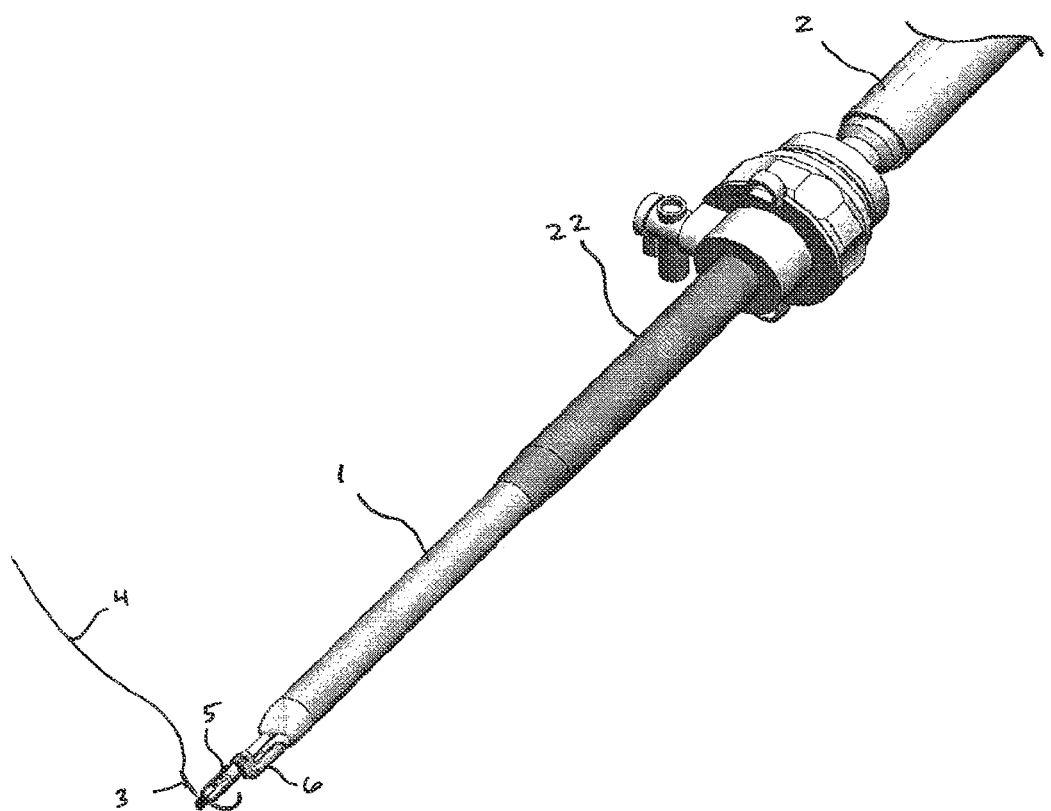
FIG. 17 shows a suturing device supporting a needle loaded with the needle loader after release or removal of the needle loader.

Once the needle holding member 110 and associated needle 3 are positioned in the needle loading position, as shown in FIG. 15, a physician may effect grasping of the needle with one or more clamps of the suturing device. As shown in FIG. 16, clamp 5 advances axially and rotates to grasp the needle 3. In the preferred embodiment, actuation of a handle of the device effects axial movement of clamp 5 toward the needle and grasping of a distal portion of the needle 3. After the needle 3 is supported by clamp 5, the needle loader 105 may be released from the device with a force sufficient to release the needle 3 from needle loader 105. Release or removal of needle loader 105 from close proximity of the clamps increases clearance allowing for suturing with the needle by clamps 5 and 6 without interference from the needle holder 105. As shown in FIG. 17, the needle loader 105 has been removed from the immediate vicinity of the clamps 5 or 6 (either by release or axial retraction into the distal portion 1) to facilitate applying suture 4 with needle 3 alternatingly supported with clamps 5 and 6.

Figure 18A:
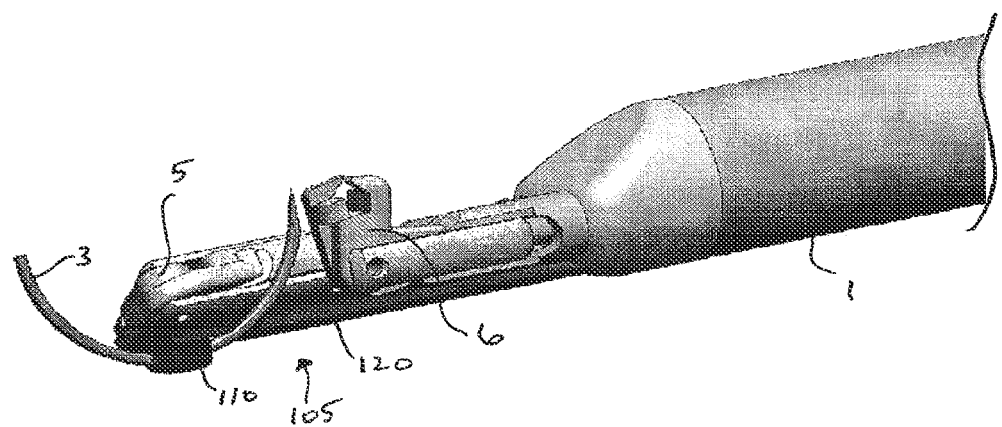
FIGS. 18A-18B shows an alternative clamp configuration of an exemplary device, wherein advancement of a clamp rotates the needle into the needle loading position.
Figure 18B:
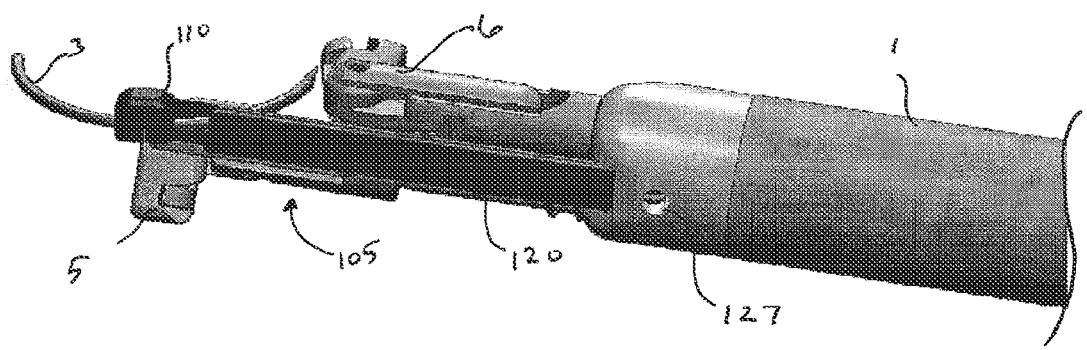

FIGS. 18A and 18B show an embodiment where the needle 3 is positioned in a pre-determined alignment within needle holding member 110 in the delivery position so that axial movement of the clamps 5 or 6 during nudges the needle 3 so as to rotate the needle holding member 110 from the needle delivery position into the needle loading position. As shown, in FIG. 18A, clamp 6 is configured to be just proximal of a portion of needle 3 when in the retracted position, such that advancement of clamp 6 nudges the needle 3 and rotates the needle 3 into the needle loading position for subsequent grasping with clamp 5.

Alternative embodiments may include an additional mechanism for rotating needle holding member 110, such as a pull wire or compression rod coupled with needle holding member 110. In such an embodiment, axial movement of the mechanism from a proximal portion of the device would effect rotation of needle holding member 110 relative to the device axis. The rotation mechanism may be separate from the mechanism for effecting grasping with the clamps or may utilize at least a portion of the mechanism used for effecting movement of the clamps. In some embodiments, the device may include a lever or button for alternating an actuation mechanism of the device between causing grasping of the clamps and axial movement and/or rotation of needle loader 105. For example, by moving a lever from a first position to a second position, the actuation mechanism of the handle may be engaged with a rod coupled to the needle holding member 110 to effect rotation of the needle holding member 110 from a delivery position to a needle loading position upon actuation of the handle.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed:

1. A suturing method comprising:
   introducing a body of a suturing device into an aperture in a patient, the body of the device extending along a device axis toward a first clamp;
   advancing a needle loader through the aperture with the needle loader supporting a needle in a delivery position providing a delivery profile, wherein the needle loader comprises:
   an elongate body coupled to a rotatable needle holding member, the needle holding member having a needle holder slot configured to receive and hold the needle, the needle holding member configured to rotate relative to the elongate body between a needle delivery position in which the needle holder slot is parallel to the elongate body, and a needle loading position in which the needle holder slot is perpendicular to the elongate body;
   wherein moving the needle into the needle loading position comprises rotating the needle from the needle delivery position to the needle loading position; and
   wherein a plane of curvature of the needle is substantially aligned with the device axis when supported with the needle loader in the delivery position, and wherein the plane of curvature of the needle is transverse to the device axis when supported with the needle loader in the needle loading position;
   moving the needle relative to the needle loader into a large profile needle loading position aligned with the first clamp;
   grasping the needle with the first clamp while the needle is supported by the needle loader in the needle loading position within the patient; and
   releasing the needle from the needle loader while the needle is supported with the first clamp.

2. The suturing method of claim 1, wherein rotating the needle comprises rotating a needle holder portion of the needle loader supporting the needle in a predetermined alignment relative to the needle holder portion.

3. The suturing method of claim 2, wherein rotating the needle comprises applying a force to a portion of the needle thereby rotating the needle holding portion of the needle loader and the needle supported therein.

4. The suturing method of claim 3, wherein applying a force to a portion of the needle comprises pushing the needle against a tissue.

5. The suturing method of claim 3, wherein applying a force to a portion of the needle comprises pushing the needle with a tool.

6. The suturing method of claim 3, wherein applying a force to a portion of the needle comprises pushing the first clamp against the needle.

7. The suturing method of claim 1, wherein moving the needle to the needle loading position comprises rotating the needle supported in the needle loader until the plane of curvature of the needle is substantially perpendicular to the device axis.

8. The suturing method of claim 1, wherein moving the needle comprises manually moving a proximal portion of the device.

9. The suturing method of claim 8, wherein moving the needle from a proximal portion of the device comprises manipulating a proximal handle of the device.

10. The suturing method of claim 1, wherein releasing the needle from the needle loader comprises axially moving the needle loader away from the needle when supported with the first clamp.

11. The suturing method of claim 1, wherein the needle loader releasably couples to the body of the device with a coupling member, and wherein releasing the needle from the needle loader comprises de-coupling the coupling member.

12. The suturing method of claim 11, wherein releasing the needle loader from the body of the device comprises applying a force on the needle loader with a tool thereby de-coupling the coupling member.

13. The suturing method of claim 1, wherein grasping the needle with the first clamp comprises grasping a base portion of the needle with the first clamp, the needle having a needle axis extending from the base portion to a tissue penetrating portion having a sharp end, said method further comprising:
   after releasing the needle from the needle loader, inserting the sharp end of the needle through a tissue of the patient while the first clamp holds the needle and after release of the needle from the needle loader;
   grasping the tissue penetrating portion of the needle with a second clamp of the suturing device;
   releasing the base portion of the needle from the first clamp; and
   pulling the base portion of the needle through the tissue while the second clamp holds the needle by moving the second clamp relative to the tissue.

14. The suturing method of claim 13, wherein inserting the needle comprises moving the body of the device while the first clamp holds the needle at a substantially fixed location relative to the body of the device.

15. The suturing method of claim 13, wherein pulling the base end of the needle comprises pulling the needle by moving the body of the device while the second clamp holds the needle at a substantially fixed location relative to the body of the device.

16. The suturing method of claim 13, wherein inserting the sharp end of the needle through the tissue and pulling the base end of the needle through the tissue each comprise moving the body of the suturing device by a physician manually holding a proximal portion of the suturing device.

17. The suturing method of claim 13, wherein releasing the needle from the needle holder is effected by manually actuating a mechanism on the proximal portion of the body of the device.

18. The suturing method of claim 13, wherein the grasping and releasing steps are effected by manually actuating a handle of the suturing device with a hand of a surgeon.

19. The suturing method of claim 13, wherein grasping and releasing of the clamps are effected by moving a handle between a first configuration relative to the body and a second configuration relative to the body, movement of the handle from the first configuration to the second configuration and back to the first configuration defining a handle actuation cycle, and wherein the needle alternates at least once between being supported by the first clamp and being supported by the second clamp with each handle actuation cycle.

20. The suturing method of claim 1, wherein the needle loader is coupled with the body of the suturing device such that introducing the body of the suturing device concurrently advances the needle loader to the surgical site.

21. The suturing method of claim 1, wherein advancing the needle loader comprises advancing the needle loader through the body of the suturing device, wherein the needle loader is slidably positionable within the body of the device.

22. The suturing method of claim 1, said method further comprising:
   selecting a needle from a plurality of standard surgical needles;
   coupling the needle with the needle loader so that the needle is releasably supported with the needle loader; and
   coupling the needle loader supporting the needle to the distal portion of the device body to facilitate introduction of the needle to the surgical site and loading of the needle for suturing.

23. The suturing method of claim 1, said method further comprising:
   selecting a needle from a plurality of standard surgical needles, each of the plurality of needles releasably supported with a needle loader;
   coupling the needle loader supporting the selected needle with the body of the device to facilitate introduction of the needle to the surgical site and loading of the needle for suturing.

24. An endoscopic suturing device for use with a suturing needle to suture a target tissue of a patient accessible via a surgical aperture, the device comprising:
   a body having a proximal portion and a distal portion with a device axis extending therebetween;
   a first clamp disposed near the distal portion and operatively coupled to the body such that, when actuated from the proximal portion of the device, the first clamp grasps the needle when the needle is in a needle loading position;
   a needle loader coupleable to the body and releasably supporting the needle with the needle movable within the patient between a needle delivery position and a needle loading position, wherein the needle loader comprises:
   an elongate body coupled to a rotatable needle holding member, the needle holding member having a needle holder slot configured to receive and hold the needle, the needle holding member configured to rotate relative to the elongate body between a needle delivery position in which the needle holder slot is parallel to the elongate body, and a needle loading position in which the needle holder slot is perpendicular to the elongate body;
   wherein, in the needle delivery position, the needle has a delivery profile to facilitate introduction of the needle through the aperture, and
   wherein, in the needle loading position, the needle has a larger profile and is aligned with the first clamp to facilitate grasping with the first clamp within the patient for suturing of the target tissue with the needle; and wherein a plane of curvature of the needle is substantially aligned with the device axis when supported with the needle loader in the needle delivery position, and wherein the plane of curvature of the needle is transverse to the device axis when supported with the needle loader in the needle loading position.

25. The suturing device of claim 24, further comprising:
a second clamp disposed near the distal portion and operatively coupled to the body such that, when actuated from the proximal portion of the device, the second clamp grasps the needle when aligned with the second clamp;
a linkage effecting movement of each of the first and second clamps between a retracted position and a grasping position by axial and rotation movement of each of the first and second clamps, wherein each clamp is rotated laterally away from the needle and retracted proximally away from the needle in the retracted position to increase clearance between the retracted clamp and the tissue and/or needle.

26. The suturing device of claim 25, wherein at least one of the first or second clamp is positioned such that axial movement of the first or second clamp when moving from the retracted position to the grasping position pushes a portion of the needle so as to rotate the needle holder from the delivery position to the needle loading position.

27. The suturing device of claim 26, further comprising a chamfered projection disposed on at least one of the first or second clamps such that the chamfered projection nudges the needle supported by the needle holder into the needle loading position when the clamp is moved axially along the device axis.

28. The suturing device of claim 24, wherein the plane of curvature of the needle is substantially perpendicular to the device axis when supported with the needle loader in the needle loading position.

29. The suturing device of claim 24, wherein the elongate body is positionable near the distal portion of the body of the device.

30. The suturing device of claim 29, wherein the needle holding member rotates between the delivery position and the needle loading position when a force is applied to a portion of the needle when supported within the needle holding member.

31. The suturing device of claim 29, wherein a proximal portion of the elongate body is releasably coupleable with the distal portion of the body of the device.

32. The suturing device of claim 29, wherein the rotatable needle holding member has a 90 degree range of rotational motion.

33. The suturing device of claim 29, wherein the needle holding member is pivotally coupled near a distal portion of the elongate body.

34. The suturing device of claim 29, wherein rotation of the needle holding member in one direction terminates in the needle delivery position, and wherein rotation of the needle holding member in the opposite direction terminates in the needle loading position.

35. The suturing device of claim 29, wherein the needle receiving slot is dimensioned so as to secure the needle with an interference fit.

36. The suturing device of claim 29, wherein the needle receiving slot is dimensioned so as to secure the needle with a resilient snap fit.

37. The suturing device of claim 29, wherein the elongate body comprises a needle receiving notch in a side of the elongate body for supporting a portion of the needle when supported with the needle holding member in the delivery position.

38. The suturing device of claim 37, wherein the needle receiving notch of the elongate body faces in the opposite direction as the needle receiving slit of the needle holding member when positioned in the needle delivery position so as to further secure the needle in the delivery position and inhibit loss of the needle during delivery.

39. The suturing device of claim 29, wherein the distal portion of the device body comprises a distal aperture for receiving the proximal portion of the elongate body for coupling to the body of the device.

40. The suturing device of claim 39, wherein the proximal portion of the elongate body comprises a coupling member for coupling with the device.

41. The suturing device of claim 40, wherein the coupling member comprises a bulbous or spherical feature that interfaces with a receiving feature of the device body.

42. The suturing device of claim 41, wherein the receiving feature of the device body comprises a side hole for receiving the bulbous or spherical feature so as to securely couple the elongate body in a pre-determined alignment when the needle loader when coupled to the body of the device.

43. The suturing device of claim 40, wherein the coupling member is releasably coupleable with the distal portion of the body of the device.

44. The suturing device of claim 40, wherein the coupling member is coupleable with a rod extending along the body of the device such that axial movement of the rod effects axial movement of the needle loader relative the first clamp.

* * * * *